(12) United States Patent
Sato et al.

(10) Patent No.: US 8,940,318 B2
(45) Date of Patent: Jan. 27, 2015

(54) HYDROGEL CONTACT LENS FOR SUSTAINED DRUG RELEASE AND DRUG RELEASE METHOD USING HYDROGEL CONTACT LENS FOR SUSTAINED DRUG RELEASE

(75) Inventors: Takao Sato, Tokyo (JP); Toru Matsunaga, Tokyo (JP); Aya Ichinokawa, Tokyo (JP); Osamu Sakai, Kobe (JP)

(73) Assignees: Seed Co., Ltd., Tokyo (JP); Senju Pharmaceutical Co., Ltd., Osaka-Shi (JP)

( * ) Notice: Subject to any disclaimer, the term of this patent is extended or adjusted under 35 U.S.C. 154(b) by 149 days.

(21) Appl. No.: 13/202,547

(22) PCT Filed: Jan. 15, 2010

(86) PCT No.: PCT/JP2010/050431
§ 371 (c)(1), (2), (4) Date: Aug. 19, 2011

(87) PCT Pub. No.: WO2010/095478
PCT Pub. Date: Aug. 26, 2010

(65) Prior Publication Data
US 2011/0306661 A1    Dec. 15, 2011

(30) Foreign Application Priority Data

Feb. 20, 2009 (JP) ................... 2009-037862

(51) Int. Cl.
| | |
|---|---|
| A61K 9/00 | (2006.01) |
| A61F 2/00 | (2006.01) |
| A61K 9/14 | (2006.01) |
| A61K 31/21 | (2006.01) |
| G02B 1/04 | (2006.01) |
| G02C 7/04 | (2006.01) |
| A61F 9/00 | (2006.01) |

(52) U.S. Cl.
CPC    G02B 1/043 (2013.01); G02C 7/04 (2013.01); A61K 9/0048 (2013.01); A61F 9/0017 (2013.01); Y10S 514/912 (2013.01)
USPC ............ 424/429; 424/427; 424/487; 514/912

(58) Field of Classification Search
CPC ..... A61F 9/0017; A61K 9/0048; G02B 1/043
See application file for complete search history.

(56) References Cited

U.S. PATENT DOCUMENTS

| | | | |
|---|---|---|---|
| 5,391,669 A | | 2/1995 | Sulc et al. |
| 6,265,465 B1 | * | 7/2001 | Benz et al. .................... 523/106 |
| 6,361,768 B1 | * | 3/2002 | Galleguillos et al. ....... 424/70.12 |
| 2003/0087022 A1 | * | 5/2003 | Borazjani et al. ............... 427/2.1 |
| 2006/0012751 A1 | * | 1/2006 | Rosenzweig et al. ..... 351/160 R |
| 2006/0187410 A1 | * | 8/2006 | Sato et al. ................. 351/160 R |
| 2009/0269391 A1 | * | 10/2009 | Bango et al. .................. 424/429 |

FOREIGN PATENT DOCUMENTS

| | | |
|---|---|---|
| JP | 6-508858 A | 10/1994 |
| JP | 2004-107253 A | 4/2004 |
| JP | 2004-307574 A | 11/2004 |
| WO | WO 03/090805 A1 | 11/2003 |

OTHER PUBLICATIONS

Taylor, G, and Shivalkar PR, Clinical allergy, 1971, vol. 1, p189-198.*
Uchida et al. (Azulene incorporation and release by hydrogel containing methacrylamide propyltirmenthylammonium chloride, and its application to soft contact lenses, 2003, Journal of Controlled Release, vol. 92, pp. 259-264).*
International Search Report, PCT/JP2010/050431, Mar. 16, 2010.

* cited by examiner

Primary Examiner — Kevin K. Hill
Assistant Examiner — Mark V Stevens
(74) Attorney, Agent, or Firm — Birch, Stewart, Kolasch & Birch, LLP

(57) ABSTRACT

Disclosed is a sustainedly drug-releasing hydrogel contact lens which can sustainedly release an anionic medicament such as an allergy-treating agent in a mildly irritating and effective manner while achieving vision correction. Specifically disclosed is a hydrogel comprising ionic monomers composed of at least a cationic monomer and an anionic monomer, wherein the component ratio of the ionic monomers is 5 to 20 mol % inclusive relative to the total amount of monomers that constitute the gel, and the content of the anionic monomer is 15 to 25 mol % inclusive relative to the content of the cationic monomer.

4 Claims, 1 Drawing Sheet

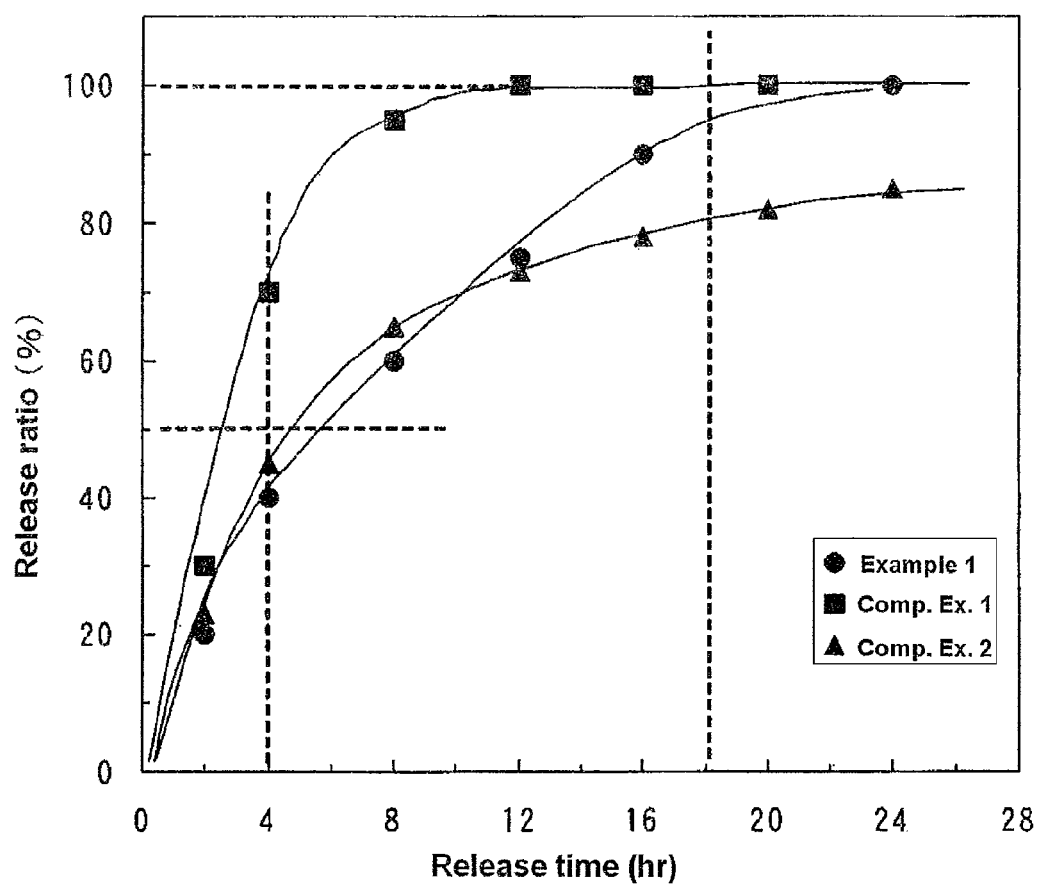

HYDROGEL CONTACT LENS FOR SUSTAINED DRUG RELEASE AND DRUG RELEASE METHOD USING HYDROGEL CONTACT LENS FOR SUSTAINED DRUG RELEASE

TECHNICAL FIELD

The present invention relates to a hydrogel contact lens for sustained drug release and a drug release method using the hydrogel contact lenses for sustained drug release. More particularly, the present invention relates to a hydrogel contact lens for sustained drug release that can suitably be used as a daily disposable contact lens that can release an anionic ophthalmic drug effectively in a relatively short period of time and a drug release method using the contact lens. As cross reference to other applications, the present application claims a benefit of priority from Japanese Patent Application No. 2009-037862, filed on Feb. 20, 2009, the entire contents of which are incorporated herein by reference.

BACKGROUND ART

The number of contact lens wearers has reached to 16 millions and contact lenses have been widely acknowledged as one of the most popular types of medical equipment. Hydrogel contact lenses take 70% or more of the contact lens market and daily-disposable-typed hydrogel contact lenses have the largest share among hydrogel contact lenses. Generally, daily-disposable-typed hydrogel contact lens wearers can wear contact lenses for 18 hours a day at longest.

Ophthalmic disorders include glaucoma, various infectious diseases and allergies. Particularly, seasonal eye allergies, pollen allergy in particular, are widely observed in daily lives and there is a large demand for easy and effective therapies against the eye allergies. Sodium cromoglycate in the form of eye-drops has been popularly used as a drug for treating eye allergies but, this drug is irritating to eyes when administered so that the drug needs to be used to alleviate the irritating side effect of the drug by adding a refreshing agent, a mucopolysaccharide and the like to the drug (see JP 2004-59583 A and JP 2005-187407 A, the disclosures of which are incorporated herein by reference).

JP 2004-59583 A discloses a technique of alleviating the irritating and foreign-body feelings of a drug containing sodium cromoglycate by compounding the drug with a refreshing agent, while JP 2005-187404 A describes a technique of raising the viscosity of lacrimal fluid by means of an additive of mucopolysaccharide to suppress the absorption of sodium cromoglycate and alleviate the irritation of eyes. However, these techniques cannot satisfactorily alleviate the irritating effect of sodium cromoglycate and thus one or more other drugs need to be added in actual use.

Meanwhile, various techniques of preventing allergies including pollen allergy by using a drug for preventive administration have been discussed. For example, there has been a report that the itchiness due to eye allergies can be suppressed by administering a drug for treating allergy in the form of eye-drops before an occurrence of allergy. However, even if patients who accept suspension of wearing contact lenses and administration of eye-drops after an occurrence of allergy they may, more often than not, be reluctant to suspend wearing contact lenses and to accept administration of eye-drops before an occurrence of allergy. Thus, the preventive therapies of administering a drug for treating seasonal allergy in the form of eye-drops in advance have not become popular.

When contact lens wearers suffer from eye diseases, they need to suspend wearing contact lenses and receive the treatment with use of eye-drops, which is very dissatisfying to them because they have to give up the correction of eyesight during the treatment. For the purpose of dissolving the dissatisfaction, techniques of administering a therapeutic drug by causing contact lenses to contain the therapeutic drug have been disclosed (see JP 2004-307574 A and JP 2003-301014 A, the contents of which are incorporated herein by reference). These techniques are designed to control the release of the therapeutic drug by way of an ion exchange reaction between the components of the contact lens material and the ingredients of the therapeutic drug. JP 2004-307574 A discloses a contact lens for sustained drug release that gradually releases, as the therapeutic drug, an anionic drug having a carboxyl group, a sulfo group and a phosphate group in a molecule, wherein a cationic monomer is used as a component of hydrogel by 2 to 50 mol % and an anionic monomer is compounded with the cationic monomer by 30 to 90 mol %. JP 2003-301014 A discloses a lens for an eye for sustained drug release, wherein the lens is an ionic lens made of a copolymer of a hydrophilic monomer and a methacrylate having a phosphate group in a side chain and also has a cationic substituent in the inside of the polymer.

In the case where a contact lens as described in JP 2004-307574 A or JP 2003-301014 A is used for drug release control, it is characterized in that the ion interactions are strong so that the release rate can be slowed down, which is effective for slowly releasing a drug for a long period of time, at least over 24 hours. However, when the lens is used as daily disposable contact lens that is to be worn for about 18 hours at longest and then discarded, it cannot be expected to provide a remarkable therapeutic effect and hence is not practically feasible.

DISCLOSURE OF THE INVENTION

Problem to be Solved by the Invention

The inventors of the present invention achieved the present invention in view of the above-identified problem. An object of the present invention is to provide a technique of effectively administering an drug for treating allergies directed to seasonal eye disease with lower irritation. More specifically, an object of the present invention is to provide a hydrogel contact lens for sustained drug release that can effectively release an anionic drug such as a therapeutic drug for treating allergies with lower irritation, while correcting the eyesight of the lens wearer. More particularly, an object of the present invention is to provide a hydrogel contact lens for sustained drug release that can release a dose of a therapeutic drug for treating allergies in a relatively short period of time and hence that is suitable for being used as daily disposable contact lens.

Means for Solving the Problem

According to the invention, there is provided a hydrogel contact lens for sustained drug release of sustainedly releasing a dose of drug, wherein the amount of initial release in a time period of about 4 hours after the start of wearing the hydrogel contact lens for sustained drug release is not more than 50% of the dose of the drug contained in the hydrogel contact lens for sustained drug release, and not less than 80% of the dose of the drug contained in the hydrogel contact lens for sustained drug release is released at least in 14 hours after the start of wearing the hydrogel contact lens for sustained drug release.

More specifically, in the hydrogel contact lens for sustained drug release according to the present invention, the hydrogel comprises at least ionic monomers including a cationic monomer and an anionic monomer, the component ratio of the ionic monomers is not less than 5 mol % and not more than 20 mol % relative to the total quantity of the monomers composed in the hydrogel, and the content ratio of the anionic monomer is not less than 15 mol % and not more than 25 mol % relative to the cationic monomer.

The hydrogel contact lens for sustained drug release according to the present invention contains an anionic drug having at least one or more carboxyl groups by 0.5 to 5.0 mg.

In the hydrogel contact lens for sustained drug release according to the present invention, the anionic drug is sodium cromoglycate or potassium cromoglycate.

Advantages of the Invention

According to the present invention, there is provided a hydrogel contact lens for sustained drug release of sustainedly and effectively releasing a dose of an therapeutic drug for treating allergies with lower irritation, while correcting the eyesight of the lens wearer. Therefore, in the case of seasonal eye diseases such as pollen allergy, an therapeutic drug for treating allergies can be administered to a patient wearing contact lenses before an occurrence of allergy so that the patient can easily comply with a prescription for drug administration even in the time when the patient has lower motivation on the therapy of allergy, and hence the patient can be preventively treated against allergy in safe. Particularly, according to the present invention, a dose of an therapeutic drug for treating allergies is effectively and completely released in about 18 hours so that a contact lens according to the present invention can be feasibly used as a daily disposable contact lens.

BRIEF DESCRIPTION OF THE DRAWING

FIG. 1 is a graph showing the release ratio of sodium cromoglycate in an eye.

BEST MODE FOR CARRYING OUT THE INVENTION

The inventors of the present invention achieved this invention after examining various possible methods for releasing an appropriate amount of an anionic drug to be used as allergy therapy in an appropriate release time as well as minimizing the irritation to eyes.

Firstly, the inventors of the present invention examined various methods for controlling the amount of initial release of each of a variety of anionic drugs including sodium cromoglycate that can be used to relieve allergies such as pollen allergy but are irritating to eyes.

Normally, in the process of releasing an anionic drug from a contact lens, the drug contained at and near the surface of the contact lens is quickly released into lacrimal fluid and subsequently the anionic drug that is interacting with the cationic group in the lens material is isolated by an ion exchange reaction with the negative ion component in lacrimal fluid so that the drug is released in a sustained manner. The time of sustained release and the quantity that is released during that time vary as a function of the behavior of the contained drug in the lens but can be controlled by the crosslink density of the material.

Therefore, the inventors tried to control the release of the drug contained at and near the surface of the lens and the release of the drug immediately after the start of wearing the lens, for the control of the amount of initial release.

As a result of intensive research efforts, it was found that controlling the amount of initial release in a period between immediately after the start of wearing the contact lens and about 4 hours after the start of wearing the contact lens is effective. More specifically, it is effective that the amount of initial release of the anionic drug contained in the contact lens is limited to ½ or less of the total quantity of the drug contained in the contact lens and the remaining drug is released gradually. In view of application of the present invention to a daily disposable contact lens, the remaining drug is preferable to be completely released in a period between about 14 hours and 18 hours after the start of wearing the contact lens.

A hydrogel contact lens for sustained drug release according to the present invention is made of hydrogel comprising at least ionic monomers including a cationic monomer and an anionic monomer. The component ratio of the ionic monomers is not less than 5 mol % and not more than 20 mol % relative to the total quantity of the monomers composed in the hydrogel. The content ratio of the anionic monomer is not less than 15 mol % and not more than 25 mol % relative to the cationic monomer.

Ionic monomers that can be used for the purpose of the present invention include cationic monomers that can be dissociated into cations and anionic monomers that can be dissociated into anions.

Anionic monomers that can be used for the purpose of the present invention are not subjected to any particular limitations so long as they are monomers having a substituent referred to as a so-called anionic group such as a carboxyl group, a phosphate group or a sulfo group. Examples of such monomers include (meth)acrylic acid, methacryloxyethyl succinic acid, (meth)acryloyloxymethyl phosphate and (meth)acryloyloxymethyl phosphate. Methacryloxyethyl succinic acid is particularly preferable.

Cationic monomers that can be used for the purpose of the present invention are not subjected to any particular limitations so long as they are monomers having a substituent referred to as so-called cationic group including an ammonium group which may be a tertiary amino group, a guanidino group or an amidino group, a quaternary ammonium group, a sulfonium group, an oxonium group and a phosphonium group. Examples of cationic monomers include vinylbenzyl trialkyl ammonium salts (ammonium chloride in particular) such as vinylbenzyl dimethylpentyl ammonium salt, vinylbenzyl dimethyl n-butyl ammonium salt, methacrylamide propyl trimethyl ammonium chloride and vinylbenzyl triethyl ammonium salt and ethylmethacrylates (ammonium chloride in particular) such as 2-methacryloxyethyltrimethyl ammonium salt, 2-methacryloxyethyldimethylethyl ammonium salt and 2-methacryloxyethyldimethyl-n-pentyl ammonium salt. Methacrylamide propyl trimethyl ammonium chloride is particularly preferable.

The material of the hydrogel contact lens for sustained drug release according to the present invention is characterized in that the content ratio of the ionic monomers including a cationic monomer and an anionic monomer is designed so as to be not less than 5 mol % and not more than 20 mol % relative to the total quantity of the monomers composed in the hydrogel contact lens for sustained drug release. While the quantity of the anionic drug contained in the contact lens can be increased when the content ratio of the ionic monomers of the lens material exceeds 20 mol %, the larger content ratio of the ionic monomers increases the water content ratio of the contact lens to reduce the crosslink density so that it may be difficult to control the sustained drug release and almost all the anionic drug may be released in a short period of time of about 3 hours. Additionally, the quantity of the anionic drug that can be contained in the hydrogel contact lens for sustained drug release falls when the content ratio of the ionic monomers goes below 5 mol % so that it may no longer be possible to effectively release the drug. The water content ratio of the contact lens also may become insufficient to make the contact lens unable to feasibly function as soft contact lens.

Additionally, the hydrogel contact lens for sustained drug release according to the present invention is characterized in that the content ratio of the anionic monomer in the ionic monomers that takes 20 mol % of the contact lens is designed so as to be not less than 15 mol % and not more than 25 mol % relative to the cationic monomer. Thus, the interaction of the contact lens with the anionic drug can be effectively formed as the cationic monomer is excessively contained in the contact lens relative to the anionic monomer.

The amount of the cationic group in the contact lens in excess can be adjusted within the content ratio of the anionic monomer that is between 15 and 25 mol %. Then, as a result, the quantity of the anionic drug contained in the contact lens can be appropriately selected.

The release control of the drug is influenced not only by the content ratio of the ionic monomers but also by the intermolecular crosslink of the material of the contact lens. When the content ratio of the ionic monomers composed in the hydrogel contact lens for sustained drug release is not less than 5 mol % and not more than 20 mol %, the water content ratio of the contact lens falls so that the drug release control effect due to the crosslink density becomes optimally expressive.

As the content ratio of the ionic monomers rises, it becomes difficult to control the sustained drug release of the contact lens and the anionic drug may be mostly released in a short period of time of about 4 hours because the water content ratio of the contact lens rises to reduce the crosslink density. Then, the object of the present invention of making the contained anionic drug to be released by not more than ½ in 4 hours after the start of wearing the contact lens is no longer achievable.

It is preferable that the content ratio of the anionic monomer in the various ionic monomers contained in the contact lens is designed so as to be not less than 15 mol % and not more than mol % relative to the cationic monomer. When a drug is simply to be released over a long period of time, it is sufficient to use a cationic monomer as a component of hydrogel by 2 to 50 mol % and compound an anionic monomer relative to the cationic monomer by 30 to 90 mol % as disclosed in JP 2004-307574 A. The contact lens made with the arrangement is, however, not preferable for a daily disposable contact lens because it is not in line with the objects of the present invention. In case where the hydrogel contact lens for sustained drug release according to the present invention is used as a daily disposable contact lens, all the anionic drug contained in the contact lens is not released but a significant part thereof may be left in the contact lens.

The drug to be used for the hydrogel contact lens for sustained drug release according to the present invention is not subjected to any particular limitations. However, the use of an anionic drug is preferable for the purpose of the present invention. A preferable anionic drug to be used for the purpose of the present invention includes one having at least one or more than one carboxyl groups in a molecule. In the case of a daily disposable contact lens that is one of the objects of the present invention, the use of an anionic drug having one or more than one carboxyl groups is preferable in view of the completion of the drug release in a period between about 14 and 18 hours.

While a drug having a carboxyl group is preferable as an anionic drug to be used for the purpose of the present invention, the drug to be used is not subjected to any particular limitations and may be an anionic therapeutic drug for treating allergy, mainly directed to seasonal eye diseases. Anionic therapeutic drugs for treating allergy that can be used for the purpose of the present invention include tranilast, acitazanolast hydrate, levocabastine hydrochloride, amlexanox and olopatadine as well as sodium cromoglycate and potassium cromoglycate. For the purpose of the present invention, an anionic drug is not limited to a therapeutic drug for treating allergy and may be an antibacterial drug selected from lomefloxacin hydrochloride, ofloxacin, norfloxacin, levofloxacin, tosufloxacin, etc., a drug for treating cataract selected from pirenoxine, glutathione, etc. or an anti-inflammatory analgesic selected from pranoprofen, bromfenac sodium, diclofenac sodium, etc. A mixture of two or more than two of the above listed drugs may also be used.

Although sodium cromoglycate is known as an effective therapeutic drug for seasonal eye disorders, pollen allergy in particular, it is highly complained by patients because of the irritation when administered. However, the present invention can dissolve the problem.

The amount of the anionic drug contained in a hydrogel contact lens according to the present invention is preferably 0.5 to 5.0 mg from the viewpoint that the drug is to be effectively and completely released in 14 to 18 hours, the transparency of the contact lens and the effect of correction of eyesight. The drug can be irritating to the eye and also give a foreign-body feeling to the eye in the initial release period after the start of wearing the contact lens when the amount of the contained anionic drug exceeds 5.0 mg, whereas the drug cannot be expected to be effective when the amount falls below 0.5 mg. When sodium cromoglycate is considered, the amount of the anionic drug is more preferably 1.0 to 3.0 mg. The amount of the drug to be taken in can be appropriately adjusted by the quantity of the cationic monomer composed in the hydrogel contact lens for sustained drug release that is provided in excess.

Since the present invention provides a technique relating to a daily disposable contact lens that can effectively release an anionic drug in 14 to 18 hours, the contact lens needs to contain a relatively small amount of an anionic drug and release the drug at a relatively high rate. For this reason, the quantity of the cationic group of the hydrogel contact lens that is provided in excess needs to be relatively small.

Monomers that can be used for the purpose of the present invention and a contact lens according to the present invention can be manufactured according to the description of JP 2004-307574 A.

Monomers that an be used for the purpose of the present invention include hydrophilic monomers, hydrophobic monomers and crosslinking monomers in addition to ionic monomers including cationic monomers and anionic monomers.

It is sufficient for a hydrophilic monomer to be used for the purpose of the present invention that soft hydrogel is obtained by hydrating the polymer that is obtained by polymerization and that, at the same time, the soft hydrogel is added in order to take in an anionic drug and has at least one or more than one hydrophilic groups in a molecule. Examples of the hydrophilic monomers include hydroxymethyl(meth)acrylate, 2-hydroxyethyl(meth)acrylate, 2-hydroxypropyl(meth)acrylate, 2,3-dihydroxypropyl(meth)acrylate, 2-polyethyleneglycol(meth)acrylate, acrylamide, 2-polypropyleneglycol (meth)acrylate, N,N-dimethylacrylamide, N,N-dimethylmethacrylamide and N-vinylpyrrolidone. Two or more than two of these hydrophilic monomers may be used in combination.

A hydrophobic monomer can be used to control the water content ratio for the purpose of controlling the sustained release of the anionic drug contained in a contact lens according to the present invention. The water content ratio, the amount of a hydrophobic drug that is taken in and the like can be adjusted by using a hydrophobic monomer. Examples of hydrophobic monomers that can be used for the purpose of the present invention include trifluoroethylmethacrylate, methacrylamide, siloxanylmethacrylate, methyl methacrylate, n-butyl methacrylate, tert-butyl methacrylate, benzyl methacrylate, ethylhexylmethacrylate and lauryl(meth)acrylate.

A crosslinking monomer can be used to form intermolecular crosslinks in the material of the contact lens. The content ratio of the crosslinking monomer is preferably not more than 10 mol % relative to the total content of the monomers composed in the hydrogel contact lens for sustained drug release. When the content ratio of the crosslinking monomer exceeds 10 mol %, the hydrogel contact lens containing the crosslinking monomer may be poorly feasible for practical use because the hydrogel contact lens become hard. Examples of crosslinking monomers that can be used for the purpose of the present invention include bifunctional compounds such as ethyleneglycol di(meth)acrylate, methylenebisacrylamide and propyleneglycol di(meth)acrylate.

A refreshing agent such as menthol can be added to a stock solution for shipment of lenses in order to make the contact lens according to the present invention more comfortable when it is worn. Menthol, camphor and the like that can be used in eye-drops can be added as the refreshing agent. When menthol is added to a stock solution for shipment, it is preferably added at a ratio of not more than 0.01% and may be added at a ratio of about 0.005% if a remarkable refreshing effect is not to be expected.

EXAMPLES

As mentioned below, the present invention is described in greater detail byway of examples. However, the present invention is by no means limited to the described examples.
(Evaluation Method)
Measurement of the Amount of Taken-In Sodium Cromoglycate In each example, the contact lens containing sodium cromoglycate was immersed in physiological salt solution for not less than 48 hours to release all the sodium cromoglycate contained in the contact lens into the physiological salt solution. After the release, the sodium cromoglycate in the physiological salt solution was quantified by means of high performance liquid chromatography (HPLC, available from JASCO CORPORATION) and the quantified value was determined as the quantity of sodium cromoglycate taken in the contact lens.
Measurement of Release Ratio of Sodium Cromoglycate in the Eye A white tame rabbit was treated to keep wearing a contact lens containing sodium cromoglycate for 4 hours and also 18 hours, and the taken-off contact lens was immersed in physiological salt solution for 48 hours to release all the remaining sodium cromoglycate contained in the contact lens into the physiological salt solution. The sodium cromoglycate released into the physiological salt solution was quantified by high performance liquid chromatography (HPLC, available from JASCO CORPORATION) and the quantified value was determined as the remaining quantity of the sodium cromoglycate taken in the contact lens. The release ratio was determined from the remaining quantity.
Shape Stability The size of the contact lens was measured by means of a contact lens projector with the contact lens in physiological salt solution before and after the release of sodium cromoglycate. As for the size change before and after the release, the contact lens was rated as "◯" when the size and shape did not change and as "x" when a size change and/or deformation was observed.
Evaluation of Comfortableness of Wearing the Contact Lens in the Initial Period of Wearing A human being was treated to wear a contact lens containing sodium cromoglycate, and the irritation and the foreign-body feeling, if any, in the initial period of wearing were evaluated.

The contact lens was rated as "◯" when the wearer felt neither any irritation nor any foreign-body feeling, but as "Δ" when the wearer felt the irritation and/or the foreign-body feeling to a slight extent and as "x" when the wearer clearly felt the irritation and/or the foreign-body feeling.
Water Content Ratio The water-containing copolymer in the contact lens was dried under reduced pressure at room temperature for a day and night, and then the weight (W2) of the copolymer was measured. Thereafter, the copolymer was immersed in pure water and fully saturated with water, and then the weight (W1) of the copolymer was measured. The water content ratio was determined from these weights by using the formula shown below.

$$\text{water content ratio(weight \%)}=[(W1-W2)/W1]\times 100$$

W1: weight when saturated with water
W2: weight when the lens was dehydrated and dried Example 1

2-hydroxyethyl methacrylate (HEMA) (46.2 g: 0.35 mol), 2-hydroxypropyl methacrylate (HPMA) (37.6 g; 0.26 mol), methacrylamide propyl trimethyl ammonium chloride (MAPTAC) (12.2 g; 0.055 mol), methacryloxyethyl succinic acid (MOESA) (3.2 g; 0.013 mol), ethyleneglycoldimethacrylate (EDMA) (0.8 g; 0.004 mol) and azo-bis-isobutylonitril (AIBN) 3000 ppm (external) were mixed to the ratio shown in Table 1 and agitated for about 1 hour, while being sufficiently subjected to nitrogen substitution. After the agitation, the monomer mixture solution was put into a contact lens forming mold and the temperature thereof was raised within a range of 50 to 100° C. for 24 hours to obtain a polymer. The obtained polymer was cooled to room temperature and taken out from the mold. Then, the polymer was immersed in distilled water at about 60° C. for about 4 hours so as to become hydrated and swollen. The contact lens was treated to contain sodium cromoglycate (DSCG) by immersing the contact lens into 10 mL of 0.05 wt % aqueous solution of sodium cromoglycate prepared in advance at 25° C. for 3 hours.

Example 2

HEMA (46.2 g; 0.35 mol) HPMA (37.6 g; 0.26 mol), MAPTAC (12.9 g; 0.058 mol), MOESA (2.5 g; 0.011 mol), EDMA (0.8 g; 0.004 mol) and AIBN 3000 ppm (external) were mixed to the ratio shown in Table 1 and agitated for about 1 hour, while being satisfactorily subjected to nitrogen substitution. After the agitation, the mixture was polymerized, hydrated and swollen, and treated to contain sodium cromoglycate as in Example 1.

Example 3

HEMA (46.2 g; 0.35 mol), HPMA (37.6 g; 0.26 mol), MAPTAC (13.3 g; 0.060 mol), MOESA (2.1 g; 0.009 mol), EDMA (0.8 g; 0.004 mol) and AIBN 3000 ppm (external) were mixed to the ratio shown in Table 1 and agitated for about 1 hour, while being satisfactorily subjected to nitrogen substitution. After the agitation, the mixture was polymerized, hydrated and swollen, and treated to contain sodium cromoglycate as in Example 1.

Example 4

HEMA (54.4 g; 0.42 mol), HPMA (37.6 g; 0.26 mol) MAPTAC (6.65 g; 0.03 mol), MOESA (1.5 g; 0.007 mol), EDMA (0.7 g; 0.003 mol) and AIBN 3000 ppm (external) were mixed to the ratio shown in Table 1 and agitated for about 1 hour, while being satisfactorily subjected to nitrogen substitution. After the agitation, the mixture was polymerized, hydrated and swollen, and treated to contain sodium cromoglycate as in Example 1.

Example 5

HEMA (41.6 g; 0.32 mol), HPMA (37.6 g; 0.26 mol) MAPTAC (24.2 g; 0.11 mol), MOESA (6.21 g; 0.027 mol), EDMA (0.8 g; 0.004 mol) and AIBN 3000 ppm (external) were mixed to the ratio shown in Table 1 and agitated for about 1 hour, while being satisfactorily subjected to nitrogen substitution. After the agitation, the mixture was polymerized, hydrated to become swollen and made to contain sodium cromoglycate as in Example 1.

Comparative Example 1

HEMA (49.1 g; 0.38 mol) HPMA (22.2 g; 0.15 mol) MAPTAC (28.9 g; 0.13 mol), MOESA (7.13 g; 0.031 mol), EDMA (0.7 g; 0.004 mol) and AIBN 3000 ppm (external) were mixed to the ratio shown in Table 1 and agitated for about 1 hour, while being satisfactorily subjected to nitrogen substitution. After the agitation, the mixture was polymerized, hydrated to become swollen and made to contain sodium cromoglycate as in Example 1.

Comparative Example 2

HEMA (40.0 g; 0.51 mol), MAPTAC (11.37 g; 0.051 mol), methacryloyloxyethyl phosphate (MOEP) (5.41 g; 0.025 mol), EDMA (0.7 g; 0.004 mol) and AIBN 3000 ppm (external) were mixed to the ratio shown in Table 1 and agitated for about 1 hour, while being satisfactorily subjected to nitrogen substitution. After the agitation, the mixture was polymerized, hydrated to become swollen and made to contain sodium cromoglycate as in Example 1.

Comparative Example 3

HEMA (51.2 g; 0.39 mol), HPMA (35.4 g; 0.24 mol), MAPTAC (6.4 g; 0.028 mol), MOESA (6.4 g; 0.028 mol), EDMA (0.6 g; 0.003 mol) and AIBN 3000 ppm (external) were mixed to the ratio shown in Table 1 and agitated for about 1 hour, while being sufficiently subjected to nitrogen substitution. After the agitation, the mixture was polymerized, hydrated and swollen, and treated to contain sodium cromoglycate as in Example 1.

Thus, the contact lenses of Examples 1 to 5 were prepared. The quantities of sodium cromoglycate they contained were made to differ from each other as a function of the quantity of the cationic monomer contained in excess by changing the total quantity of the contained ionic monomers. For each example, the quantity of the contained sodium cromoglycate, the release ratios 4 hours, 14 hours and 18 hours after the start of wearing the contact lens, as well as the shape stability were observed. It was confirmed that all the contact lenses can practically be used. In other words, each of them can release almost all the drug taken in the contact lens during the time period of being worn in a day so that it can effectively be used as contact lens for treatment.

When analyzed and evaluated as in Example 1, the shape of the contact lens of Comparative Example 1 was less stable because of an increased amount of ionic monomers. The quantity of the drug taken into the contact lens of Comparative Example 2 was not sufficient and the contact lens was not effective because the content ratio of the anionic monomer was too large relative to that of the cationic monomer. Additionally, the release time of sodium cromoglycate was not less than 24 hours and hence very long to make the contact lens unsuitable to be used as daily disposable contact lens. Since the contact lens of Comparative Example 3 did not contain any cationic group that contributes to positively take in sodium cromoglycate, the contact lens did not contain a sufficient quantity of sodium cromoglycate to show the effectiveness.

FIG. 1 shows the sodium cromoglycate release ratio of the contact lens of Example 1, that of the contact lens of Comparative Example 1 and that of the contact lens of Comparative Example 2 in the eye of the wearer.

As seen from FIG. 1, the contact lens of Example 1 was proved to be feasible for practical use as daily disposable contact lens because of the satisfactory release time of sodium cromoglycate. To the contrary, 70% of the drug contained in the contact lens of Comparative Example 1 was released in the initial 4 hours because of the increased quantity of ionic monomer contained in the contact lens. It was proved that the contact lens of Comparative Example 1 might be poorly feasible for practical use. The contact lens of Comparative Example 2 released the drug contained over a very long period of time as shown in JP 2004-307574 A. It was proved that the contact lens of Comparative Example 2 might be less feasible for practical use as daily disposable contact lens.

TABLE 1

|  | Ex. 1 | Ex. 2 | Ex. 3 | Ex. 4 | Ex. 5 | Comp. Ex. 1 | Comp. Ex. 2 | Comp. Ex. 3 |
|---|---|---|---|---|---|---|---|---|
| total quantity ratio of ionic monomers (mol %) | 9.97 | 10.10 | 10.10 | 5.14 | 19.00 | 23.28 | 12.88 | 8.13 |
| quantity ratio of anionic monomers relative to | 23.64 | 18.97 | 15.00 | 23.33 | 24.55 | 23.66 | 49.02 | 100.0 |

TABLE 1-continued

|  |  | Ex. 1 | Ex. 2 | Ex. 3 | Ex. 4 | Ex. 5 | Comp. Ex. 1 | Comp. Ex. 2 | Comp. Ex. 3 |
|---|---|---|---|---|---|---|---|---|---|
| cationic monomers (mol %) quantity of taken-in DSCG (mg) | | 2.50 | 2.80 | 4.00 | 1.20 | 2.80 | 5.50 | 0.40 | 0.002 |
| release ratio (%) | 4 hours after | 40 | 43 | 44 | 38 | 46 | 70 | 45 | 98 |
| | 14 hours after | 82 | 83 | 84 | 87 | 85 | 100 | 74 | 100 |
| | 18 hours after | 95 | 95 | 96 | 92 | 96 | 100 | 78 | 100 |
| shape stability | before release of DSCG (mm) | 14.3 | 14.4 | 14.4 | 13.8 | 14.1 | 15.4 | 14.2 | 14.0 |
| | after release of DSCG (mm) | 14.4 | 14.4 | 14.5 | 14.0 | 14.3 | deformation | 14.4 | 14.1 |
| | evaluation | ○ | ○ | ○ | ○ | ○ | x | ○ | ○ |
| evaluation of comfortableness of wearing | | ○ | ○ | ○ | ○ | ○ | Δ | ○ | x |
| water content ratio (%) | | 46.0 | 45.0 | 45.0 | 38.0 | 48.0 | 58.0 | 45.0 | 42.0 |

HEMA: 2-hydroxyethyl methacrylate (hydrophilic monomer)
HPMA: 2-hydroxypropyl methacrylate (hydrophilic monomer)
MAPTAC: methacrylamide propyl trimethyl ammonium chloride (cationic monomer)
MOESA: methacryloxyethyl succinic acid (anionic monomer)
EDMA: ethyleneglycoldimethacrylate (crosslinking monomer)
MOEP: methacryloyloxyethyl phosphate (anionic monomer)
AIBN: azo-bis-isobutylonitril (polymerization initiator)
DSCG: sodium cromoglycate (anionic drug)

The invention claimed is:

1. A daily disposable hydrogel contact lens for sustained drug release of sustainedly releasing a dose of an anionic drug, wherein the amount of initial release in a time period of about 4 hours after the start of wearing the hydrogel contact lens is not more than 50% of the dose of the anionic drug contained in the hydrogel contact lens, and not less than 80% of the dose of the anionic drug contained in the hydrogel contact lens is released at least in 14 hours after the start of wearing the hydrogel contact lens; and the hydrogel contact lens comprises at least:
   (a) an anionic drug,
   (b) a combination of (i) and (ii) as hydrophilic monomers wherein (i) is either hydroxymethyl (meth)acrylate or 2-hydroxyethyl (meth)acrylate and (ii) is either 2-hydroxypropyl (meth)acrylate or 2,3-dihydroxypropyl (meth)acrylate, and
   (c) ionic monomers including a cationic monomer and an anionic monomer, the component ratio of the ionic monomers is not less than 5 mol % and not more than 20 mol % relative to the total quantity of the monomers composed in the hydrogel, and the content ratio of the anionic monomer is 15 mol % to less than 25 mol % relative to the cationic monomer.

2. The daily disposable hydrogel contact lens for sustained drug release according to claim 1, wherein the anionic drug is an anionic drug having at least one or more carboxyl groups and the amount of anionic drug contained in the hydrogel contact lens is 0.5 to 5.0 mg.

3. The daily disposable hydrogel contact lens for sustained drug release according to claim 1, wherein the anionic drug is sodium cromoglycate or potassium cromoglycate.

4. The daily disposable hydrogel contact lens for sustained drug release according to claim 1, wherein the content ratio of the anionic monomer is 15 mol % to 24.55 mol % relative to the cationic monomer.

* * * * *